(12) United States Patent
Rottenberg

(10) Patent No.: US 10,495,516 B2
(45) Date of Patent: Dec. 3, 2019

(54) DEDICATED TRANSFORMATION SPECTROSCOPY

(71) Applicant: IMEC VZW, Leuven (BE)

(72) Inventor: Xavier Rottenberg, Leuven (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/738,798

(22) PCT Filed: Jun. 28, 2016

(86) PCT No.: PCT/EP2016/065066
§ 371 (c)(1),
(2) Date: Dec. 21, 2017

(87) PCT Pub. No.: WO2017/001437
PCT Pub. Date: Jan. 5, 2017

(65) Prior Publication Data
US 2018/0195904 A1    Jul. 12, 2018

(30) Foreign Application Priority Data

Jun. 30, 2015 (EP) ..................... 15174630

(51) Int. Cl.
*G01J 3/36* (2006.01)
*G01J 3/02* (2006.01)
(Continued)

(52) U.S. Cl.
CPC .............. *G01J 3/36* (2013.01); *G01J 3/0205* (2013.01); *G01J 3/0294* (2013.01); *G01J 3/26* (2013.01);
(Continued)

(58) Field of Classification Search
CPC .... G01J 3/36; G01J 3/32; G01J 3/0205; G01J 3/26; G01J 3/12; G01J 3/0294; G01J 3/2803; G01N 21/65
See application file for complete search history.

(56) References Cited

U.S. PATENT DOCUMENTS 5,455,421 A * 10/1995 Spears ................. G01J 3/26
250/338.4
5,493,393 A * 2/1996 Beranek ............ G01D 5/34776
356/328

(Continued)

FOREIGN PATENT DOCUMENTS

WO    2015/059353    4/2015

OTHER PUBLICATIONS

"Infiltrated Photonic Crystal Fibers for Sensing Applications", by Algorri et al. (2018).*

(Continued)

*Primary Examiner* — Mohamed K Amara
(74) *Attorney, Agent, or Firm* — McDonnell Boehnen Hulbert & Berghoff LLP

(57) ABSTRACT

The invention relates to a multi-channel spectrometer device (10) for detecting/quantifying a predetermined analyte (5) in a medium (6). The device (10) comprises an input (11) for receiving radiation (7), a first plurality of optical modulators (12) adapted for transforming the radiation (7) in accordance with a first transfer function, and a second plurality of optical modulators (13) adapted for transforming the radiation (7) in accordance with a second transfer function. The spectrometer device also comprises a detector (15) for generating output signals (4) indicative for the intensity of each transformed radiation signal. The ratio of the number of optical modulators in the first plurality and the number of optical modulators in the second plurality is determined by the ratio of a reference spectrum of the predetermined (Continued)

analyte transformed by the first transfer function and the reference spectrum transformed by the second transfer function.

23 Claims, 5 Drawing Sheets

(51) Int. Cl.
    *G01J 3/26* (2006.01)
    *G01J 3/28* (2006.01)
    *G01J 3/32* (2006.01)
    *G01N 21/65* (2006.01)

(52) U.S. Cl.
    CPC ............... *G01J 3/2803* (2013.01); *G01J 3/32* (2013.01); *G01N 21/65* (2013.01)

(56) References Cited

U.S. PATENT DOCUMENTS

| | | | |
|---|---|---|---|
| 6,282,005 B1* | 8/2001 | Thompson | H04B 10/505 359/254 |
| 6,473,556 B1* | 10/2002 | Takeuchi | G01R 31/31917 385/147 |
| 6,584,126 B2* | 6/2003 | Wang | G01J 3/26 372/20 |
| 6,614,533 B1* | 9/2003 | Hata | G01J 3/2823 250/559.07 |
| 7,245,833 B1* | 7/2007 | Volkening | H04B 10/2575 398/116 |
| 7,361,501 B2 | 4/2008 | Koo et al. | |
| 7,889,336 B2* | 2/2011 | Yankov | G01N 21/253 356/301 |
| 9,677,936 B2* | 6/2017 | Han | G01J 3/36 |
| 9,684,162 B2* | 6/2017 | Whitcomb | G01J 3/0202 |
| 9,709,442 B2* | 7/2017 | Lee | G01J 3/18 |
| 9,714,863 B2* | 7/2017 | Gotsmann | B82Y 20/00 |
| 9,778,113 B2* | 10/2017 | Englund | G01J 3/26 |
| 9,867,544 B2* | 1/2018 | Kim | G01J 3/0227 |
| 9,923,007 B2* | 3/2018 | Ockenfuss | H01L 27/1462 |
| 9,960,199 B2* | 5/2018 | Ockenfuss | H01L 27/14621 |
| 2003/0222380 A1* | 12/2003 | Katzir | G01N 21/552 264/667 |
| 2007/0077595 A1* | 4/2007 | Koo | B82Y 30/00 435/7.1 |
| 2008/0013881 A1* | 1/2008 | Welch | G02B 6/12004 385/14 |
| 2008/0049228 A1 | 2/2008 | Chan | |
| 2009/0074421 A1* | 3/2009 | Thaniyavarn | H04B 10/25758 398/116 |
| 2010/0178005 A1* | 7/2010 | Okayama | G02B 6/12007 385/50 |
| 2012/0038928 A1 | 2/2012 | Saari et al. | |
| 2012/0129269 A1* | 5/2012 | Choi | A61B 5/0075 436/164 |
| 2013/0064496 A1* | 3/2013 | Suh | G02B 6/12007 385/14 |
| 2013/0176554 A1 | 7/2013 | Loncar et al. | |
| 2013/0321816 A1* | 12/2013 | Dattner | G02B 6/125 356/451 |
| 2014/0318188 A1* | 10/2014 | Bowker | C03B 37/0253 65/378 |
| 2015/0086193 A1* | 3/2015 | Liu | H04B 10/2543 398/28 |
| 2015/0372159 A1* | 12/2015 | Englund | H01L 31/09 356/328 |
| 2016/0071689 A1* | 3/2016 | de Jong | H01J 37/28 250/307 |

OTHER PUBLICATIONS https://en.wikipedia.org/wiki/Transfer_function.*
Tarumi, Toshiyasu et al., "Multivariate Calibration with Basis Functions Derived From Optical Filters", Anal. Chem., vol. 81, 2009, pp. 2199-2207.
International Search Report and Written Opinion dated Sep. 23, 2016 for International Application No. PCT/EP2016/065066 filed Jun. 28, 2016, 14 pages.

* cited by examiner

DEDICATED TRANSFORMATION SPECTROSCOPY

The present application is a section 371 U.S. patent application claiming priority to PCT/EP2016/065066, filed Jun. 28, 2016, which claims priority from EP Application No. 15174630.2, filed Jun. 30, 2015, the contents of which are hereby incorporated by reference.

FIELD OF THE INVENTION

The invention relates to the field of spectroscopy. More specifically, it relates to devices and methods for acquiring and processing electromagnetic spectrometric data to detect a predetermined analyte of interest. In particular, the present invention relates to a multi-channel spectrometer and a method for processing spectrometric data obtained by such spectrometer.

BACKGROUND OF THE INVENTION

Spectrometry can be a useful tool for detecting and/or quantifying analytes of interest in a medium, for example for determining a glucose concentration in blood or tissue. Several types of spectrometry are known, such as for example radio-frequency, mid-infrared, near-infrared, Raman, visual spectrum or near-ultraviolet spectroscopy. For spectrometric detection and quantification, a good signal to noise ratio is desirable, e.g. such as to be able to distinguish a weak spectral signal related to the analyte of interest from a noisy background signal, e.g. containing a complex mixture of spectra of known and/or unknown chemical compounds in a known or unknown mixture composition.

In order to detect and/or quantify an analyte of interest, a method or system known in the art may probe a sample, for example a tissue, using radiation, e.g. infrared radiation. The analyte, when present in the sample, absorbs and/or interacts with the radiation in accordance with a reference spectrum of the analyte. For example, glucose absorbs radiation at known frequencies in the near-infrared and mid-infrared spectral range. However, the background interaction of other components of the sample, e.g. other analytes present in the tissue or blood sample being tested for glucose content, such as haemoglobin, may interact at similar frequencies. Therefore, a calibration procedure may be used to relate measured spectral data to the concentration of the analyte of interest. Such calibration procedure may for example involve a multivariate analysis of reference spectra obtained for reference samples having known concentrations of the analyte of interest.

For example, in Raman spectroscopy, the vibrational, rotational, and other low-frequency modes of a system are characterized by the Raman energy spectrum generated by inelastic scattering phenomena in this system, e.g. caused by the interaction of substantially monochromatic light with molecular vibrations, phonons or other excitation modes of the system. Raman spectroscopy can be particularly useful for microscopic analysis, since sectioning or fixation of the sample is not required and the spectral data can be collected from a small volume, for example a volume of about a micrometer in diameter. Furthermore, Raman spectroscopy can be used for imaging, e.g. by parallel excitation and spectral data collection over a plurality of points distributed over a sample to be imaged or by scanning an excitation beam over the sample while collecting the spectral data as function of location. Raman spectroscopy in the near-infrared electromagnetic spectrum also offers the advantage of a low risk of damaging the sample, and the possibility of non-invasive in-vivo measurements, e.g. to detect analytes of interest in tissue and blood through the skin.

However, the spectral data obtained from Raman scattering can be quite weak, e.g. distinguishing the inelastically scattered light from other light signals, such as Rayleigh scattered light, can be difficult. For example, even though Raman spectrometry may be suitable for detecting the presence of an analyte, such as for determining a glucose concentration in blood, the Raman signal for characterizing the analyte can be very weak and difficult to separate from its noisy background. Therefore, it would be advantageous to obtain low noise levels relative to the signal intensity levels obtained by a Raman spectrometer and to provide a high quality algorithm for extracting a component of interest from the acquired spectral information, e.g. to extract the glucose signal from spectral information obtained from a blood sample. Furthermore, it would also be advantageous to achieve a high throughput while obtaining Raman spectral data, e.g. while Raman imaging, and extracting information of interest from the collected spectral data.

Integrated systems for collecting spectrometric data from samples are known in the art. For example, silicon-on-insulator arrayed waveguide spectrometers are known in the art that can comprise, for example, 50 channels. However, other prior-art integrated spectrometry devices do not require a grating. For example, U.S. Pat. No. 7,361,501 discloses a spectral analyser having one or more Mach-Zehnder interferometers, a detector and a microprocessor.

Tarumi et al., "Multivariate calibration with basis functions derived from optical filters," Anal. Chem. 2009, 81, 2199-2207, disclosed a numerical optimization method to define a set of Gaussian basis functions that can be used to represent the important information in a calibration set of near-IR spectra. This may advantageously provide a lower-order basis. Furthermore, because of their analogy to optical filters with a single band-pass, the Gaussian basis functions allow the calibration model to take the form of a specialized filter photometer that is dedicated to a given analytical determination.

SUMMARY OF THE INVENTION

It is an object of embodiments of the present invention to provide good and efficient means and methods for obtaining spectral information from a sample and for detecting and quantifying a predetermined analyte of interest from this spectral information.

It is an advantage of embodiments of the present invention that the complexity, and hence the cost, for providing a spectroscopy analysis in accordance with embodiments of the present invention is equal to or of the same order of magnitude as for spectroscopy analysis approaches known in the art, e.g. other advantages as described hereinbelow can be achieved without added complexity and cost.

It is an advantage of embodiments of the present invention that a good signal-to-noise ratio (SNR) can be achieved in spectral analysis of a sample, e.g. in detecting and/or quantifying an analyte of interest, such as glucose, in a sample by Raman spectroscopy.

It is an advantage of embodiments of the present invention that a spectrometry architecture can be tuned such as to provide good detection of a predetermined analyte.

It is an advantage of embodiments of the present invention that detection and/or quantification of an analyte can be provided by a simple algorithm, e.g. by simply manipulating the spectrum in the optical domain.

It is an advantage of embodiments of the present invention that a generic spectroscopy architecture can be tuned, e.g. optimized, to provide high sensitivity, e.g. a high signal to noise ratio, with respect to detection of a specific, predetermined analyte.

It is an advantage of embodiments of the present invention that non-invasive measurements of an analyte of interest can be carried out on a biological tissue, for example a glucose in-vivo measurement on human tissue. It is a further advantage of embodiments of the present invention that accurate and precise measurements of glucose concentration can be determined non-invasively, e.g. sufficiently precise and accurate to adjust dietary intake and/or insulin dosing in diabetic patients and/or to determine hypo-glycemia and hyper-glycemia.

The above objective is accomplished by a method and device according to the present invention.

The present invention relates to a multi-channel spectrometer device for detecting and/or quantifying a predetermined analyte of interest in a medium, the spectrometer device comprising:
an input for receiving a radiation signal,
a first plurality of optical modulators operably connected to said input, each optical modulator of said first plurality of modulators being adapted for transforming said radiation signal in accordance with a first transfer function,
a second plurality of optical modulators operably connected to said input, each optical modulator of said second plurality of modulators being adapted for transforming said radiation signal in accordance with a second transfer function,
at least one detector element operably connected to said first and second plurality of optical modulators and adapted for generating a plurality of output signals indicative for the intensity of each of the plurality of transformed radiation signals of the first and the second plurality of optical modulators,
wherein the ratio of the number of optical modulators in said first plurality of optical modulators and the number of optical modulators in said second plurality of optical modulators is substantially determined by the ratio of a reference spectrum of said predetermined analyte of interest transformed by said first transfer function and said reference spectrum transformed by said second transfer function.

The ratio of the number of optical modulators in said first plurality of optical modulators and the number of optical modulators in said second plurality of optical modulators may be substantially equal to an integer power of the ratio of said reference spectrum transformed by said first transfer function and said reference spectrum transformed by said second transfer function, wherein said integer lies in the range of −10 to −1 or in the range of 1 to 10. The integer power may be the identity function or the reciprocal function.

The multi-channel spectrometer device further may comprise at least one further plurality of optical modulators, wherein the optical modulators of each further plurality of the at least one further plurality of optical modulators may be adapted for transforming the radiation signal in accordance with a further transfer function corresponding to this further plurality of optical modulators.

The multi-channel spectrometer device may be a multi-channel Raman spectrometer.

Said input may comprise a radiation coupler for coupling the radiation signal into the multi-channel spectrometer device.

The multi-channel spectrometer device furthermore may comprise a splitter for splitting the radiation signal received by the input into a plurality of waveguides, each waveguide feeding the radiation signal into a corresponding optical modulator.

The multi-channel spectrometer device may be specifically adapted for quantifying the concentration of glucose in blood.

The first plurality of optical modulators and/or the second plurality of optical modulators may comprise a photonic resonator or a photonic filter.

Said photonic resonator may comprise a Mach-Zehnder Interferometer, a Fabry-Perot cavity or a resonator ring.

The present invention also relates to a spectrometer system comprising a radiation source for illuminating a medium and a multi-channel spectrometer device as described above for detecting and/or quantifying a predetermined analyte of interest in said medium, wherein the multi-channel spectrometer device is configured to receive a radiation signal from the illuminated medium via the input of said multi-channel spectrometer device.

The spectrometer system furthermore may comprise a processing means for analyzing the plurality of output signals generated by the at least one detector element of said multi-channel spectrometer device, thereby detecting and/or quantifying said predetermined analyte of interest in said medium.

The present invention also relates to a method for detecting and/or quantifying a predetermined analyte of interest in a medium, the method comprising:
receiving a radiation signal carrying information about constituents of said medium in its spectral composition,
optically modulating said radiation signal to provide a first plurality of transformed radiation signals, each of the first plurality of transformed radiation signals being a transformation of said radiation signal in accordance with a first transfer function,
optically modulating said radiation signal to provide a second plurality of transformed radiation signals, each of the second plurality of transformed radiation signals being a transformation of said radiation signal in accordance with a second transfer function,
generating a plurality of signals indicative for the intensity of each transformed radiation signal of the first plurality and of the second plurality of transformed radiation signals, and
analyzing the plurality of signals to detect and/or quantify said predetermined analyte of interest in said medium,
wherein the ratio of the number of transformed radiation signals in said first plurality of transformed radiation signals and the number transformed radiation signals in said second plurality of transformed radiation signals is substantially determined by the ratio of a reference spectrum of said predetermined analyte of interest transformed by said first transfer function and said reference spectrum transformed by said second transfer function.

The present invention also relates to a method for designing a multi-channel spectrometer device for detecting and/or quantifying a predetermined analyte of interest in a medium, the method comprising:
obtaining a reference spectrum of said predetermined analyte of interest,
selecting a plurality of transfer functions corresponding to a plurality of optical modulators,
providing a multi-channel spectrometer device design comprising a plurality of optical modulators coupled to an input for receiving a radiation signal, wherein for each pair of said plurality of transfer functions, the ratio of the number of optical modulators having the first transfer function of said pair and the number of optical modulators having the second transfer function of said pair is determined by a ratio of the reference spectrum transformed by said first transfer function and the reference spectrum transformed by said second transfer function.

A computer program product for implementing a method as described above when executing on a computing device.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
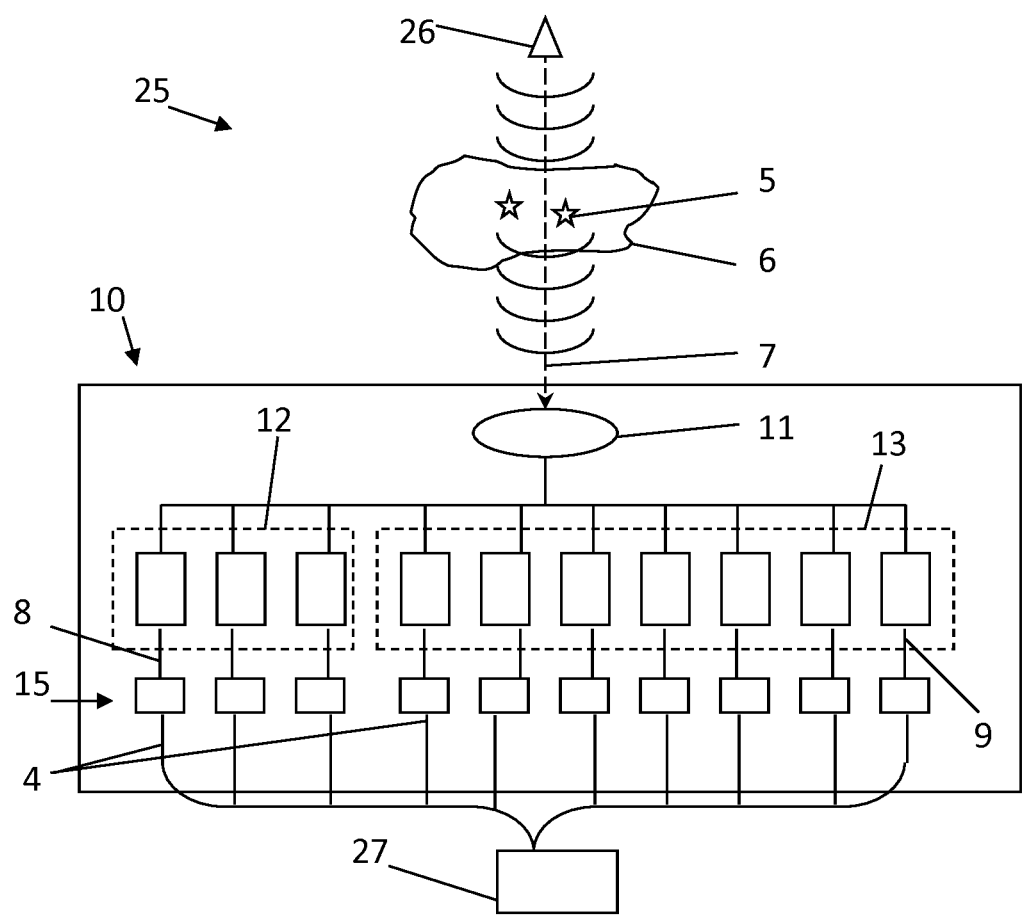
FIG. 1 shows a multi-channel spectrometer device according to embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "transfer function", reference is made to the spectral transfer function of an optical component for describing how the component projects radiation from an input signal into an output signal in terms of spectral wavelength, or equivalently in terms of temporal frequency or wavenumber. Particularly, it may relate to a representation in terms of spectral frequency or wavelength of the relation between the input and output of an optical component, e.g. a linear time-invariant optical component, with zero initial conditions and zero-point equilibrium. More particularly the transfer function may be a function $T(\lambda)$, where T represents the ratio of the output intensity over the input intensity when a monochromatic input of wavelength $\lambda$ is presented as input to the system. For example, for a component in which the output is directly related to the input via optical transmission through the component, the transfer function may be transmittance function, where for a component in which the output is directly related to the input via optical reflection phenomena, the transfer function may be a reflectance function.

Where in embodiments of the present invention reference is made to an "optical modulator", reference is made to an optical component, e.g. an integrated photonic circuit component, that transforms an input optical wave into an output optical wave by absorbing, phase modulating, reflecting, transmitting, diffracting or otherwise altering the input wave in a wavelength dependent manner.

Where in embodiments of the present invention reference is made to a "reference spectrum", reference is made to a function of optical wavelength or frequency, representing the wavelength-dependency of an interaction of electromagnetic radiation with an analyte of interest. This interaction may specifically relate to a specific interaction to which a spectrometer according to embodiments of the present invention is sensitive, e.g. is adapted for acquiring. For example, the reference spectrum may refer to a Raman spectrum or a near-infrared spectrum of the analyte. Furthermore, the reference spectrum may also relate to the spectrum of a standardized solution of the analyte of interest, e.g. the spectrum of a medium comprising the analyte in a predetermined concentration. For example, in specific embodiments of the present invention, the reference spectrum may refer to a Raman spectrum of glucose, or to a Raman spectrum of a standardized solution of glucose in water, e.g. at a well-defined and controlled predetermined concentration, or to a Raman spectrum of a standardized solution of glucose in blood, e.g. at a well-defined and controlled predetermined concentration.

In a first aspect, the present invention relates to a multi-channel spectrometer device for detecting and/or quantifying a predetermined analyte of interest in a medium. The multi-channel spectrometer device comprises an input for receiving a radiation signal. The multi-channel spectrometer device also comprises a first plurality of optical modulators operably connected to the input and a second plurality of optical modulators operably connected to the input. Each optical modulator of the first plurality of modulators is adapted for transforming the radiation signal in accordance with a first transfer function, e.g. each modulator of the first plurality of modulators having substantially the same transfer function. Each optical modulator of the second plurality of modulators is adapted for transforming the radiation signal in accordance with a second transfer function, the second transfer function being substantially different, e.g. different, from the first transfer function. For example, each modulator of the second plurality of modulators has substantially the same transfer function, this transfer function being different from the transfer function of modulators of the first plurality of modulators. The second plurality of modulators and the first plurality of modulators are disjunct sets, e.g. they relate to different modulators, e.g. the first plurality and the second plurality do not comprise optical modulators shared between both sets. The multi-channel spectrometer device further comprises at least one detector element operably connected to the first plurality of optical modulators and to the second plurality of optical modulators. The at least one detector element is adapted for generating a plurality of output signals indicative of the intensity of each of the plurality of transformed radiation signals of the first and the second plurality of optical modulators. The ratio $r=N_1/N_2$ of the number $N_1$ of optical modulators in the first plurality of optical modulators and the number $N_2$ of optical modulators in the second plurality of optical modulators is substantially determined, e.g. is determined, by the ratio of a reference spectrum of the predetermined analyte of interest transformed by the first transfer function and this reference spectrum transformed by said second transfer function. Thus, the ratio having as numerator the number of optical modulators in the first plurality of optical modulators and as denominator the number of optical modulators in the second plurality of optical modulators is substantially determined, e.g. is determined, by the ratio having as numerator a reference spectrum of the predetermined analyte of interest transformed by the first transfer function and as denominator this reference spectrum transformed by the second transfer function.

FIG. 1 schematically shows a multi-channel spectrometer device 10 according to embodiments of the present invention. In embodiments of the present invention, the multi-channel spectrometer device may be a Raman spectrometer or an infrared spectrometer. The multi-channel spectrometer may have a transform spectrometer architecture, for example a Fourier transform spectrometer architecture. The multi-channel spectrometer 10 may be an integrated circuit device, e.g. an integrated photonic circuit.

Particularly, in embodiments according to the present invention, the multi-channel spectrometer device may comprise a plurality of channels adapted for extracting, e.g. for measuring, a component of the spectrum of the radiation signal 7, e.g. of a radiation signal 7 carrying information about properties of constituents of a medium 6 in its spectral composition. For example, each such channel may comprise a radiation propagation path from the input 11 through an optical modulator, e.g. an optical modulator of the first plurality of optical modulators 12 or of the second plurality of optical modulators 13, to a detector element of the plurality of detector elements 15. Thus, the component being extracted by the channel may be determined by the transfer function of the corresponding optical modulator. The output signals indicative of the intensity of each of the plurality of transformed radiation signals of the first and the second plurality of optical modulators may thus be considered as a set of components corresponding to a set of basis functions on which the spectrum of the input 11 is projected, in which the transfer functions of the optical components correspond to these basis functions. Where reference is made to basis functions, these basis functions may not form a basis in the literal mathematical sense, e.g. may not be a set of orthonormal functions, but may approximate such set of orthonormal, or at least orthogonal, functions within the limits imposed by the physical properties of the optical components, e.g. where a mathematical basis may comprise functions having infinite slope edges and/or negative values over at least part of their domain, such functions may be approximated by transfer functions having sharp slope edges and/or having an additive constant offset with respect to the basis function to ensure positive values over its entire domain.

This multi-channel spectrometer device may be specifically adapted for detecting the presence of a predetermined analyte 5 of interest in a medium 6. Alternatively or additionally, the multi-channel spectrometer device may be adapted for quantifying the concentration of the predetermined analyte 5 of interest in the medium 6. The multi-channel spectrometer device may for example be adapted for detecting a predetermined molecule, compound or ion. For example, the multi-channel spectrometer device may be adapted for detecting a predetermined protein, antibody, metabolite or nucleic acid in a biological sample or tissue. The multi-channel spectrometer device may be adapted to determine the concentration of such analyte in a medium comprising a mixture of other known and/or unknown components. For example, the medium may comprise other components in unknown concentrations which contribute to the signal in the form of nuisance variables, e.g. which may be considered as sources of noise in determining the presence and/or concentration of the analyte of interest.

The multi-channel spectrometer device according to embodiments of the present invention may be specifically adapted for quantifying the concentration of glucose, e.g. the predetermined analyte of interest being glucose, in blood, e.g. the medium 6 being blood.

The multi-channel spectrometer device 10 comprises an input 11 for receiving a radiation signal 7, e.g. for receiving a radiation signal spectrally conveying information regarding the composition of the medium. For example, the input 11 may comprise a radiation coupler, e.g. a grating coupler, for coupling the radiation signal 7 into the spectrometer device 10, e.g. into an integrated photonic circuit forming the spectrometer device. The multi-channel spectrometer device 10 may also comprise a splitter, e.g. a radiation splitter, e.g. an integrated photonic radiation splitter, for splitting the radiation signal 7 received by the input 11, e.g. coupled into the device by the radiation coupler, into a plurality of waveguides, in which each such waveguide feeds the radiation signal into a corresponding optical modulator, e.g. an optical modulator of the first or second plurality of optical modulators 11,12.

Figure 2:
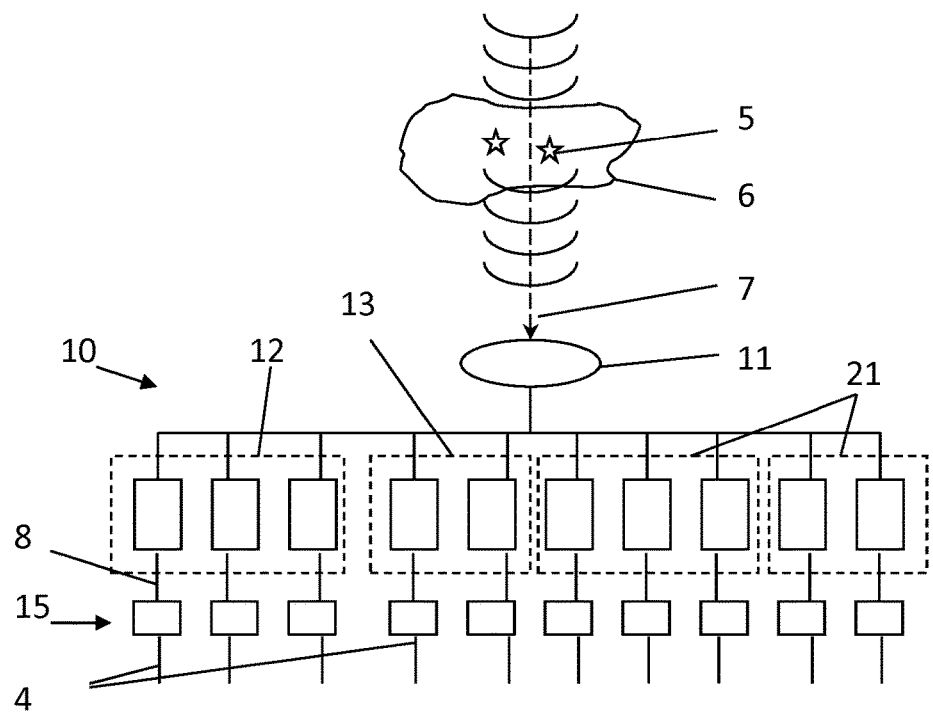
FIG. 2 shows another multi-channel spectrometer device according to embodiments of the present invention.

The multi-channel spectrometer device 10 further comprises a first plurality of optical modulators 12 operably connected to the input 11 and a second plurality of optical modulators 13 operably connected to the input 11. The multi-channel spectrometer 10 may further comprise at least one further plurality of optical modulators 21, e.g. as shown in FIG. 2. Each at least one further plurality of optical modulators 21 may be operably connected to the input 11. For example, the multi-channel spectrometer device 10 may comprise a splitter, e.g. an integrated photonic radiation splitter, for splitting the radiation signal 7 received by the input 11 into a plurality of waveguides, in which each such waveguide feeds the radiation signal into a corresponding optical modulator of the first, second or any further plurality of optical modulators 11,12,21. For example, the multi-channel spectrometer may comprise a plurality of channels partitioned in a plurality of groups, each group corresponding to the first plurality, the second plurality or a further plurality of optical modulators.

Each optical modulator of the first plurality of modulators 12 is adapted for transforming the radiation signal 7 in accordance with a first transfer function. Likewise, each optical modulator of the second plurality of modulators 12 is adapted for transforming the radiation signal 7 in accordance with a second transfer function, e.g. a transfer function distinct from the first transfer function. In embodiments comprising at least one further plurality of optical modulators 21, e.g. as shown in FIG. 2, the optical modulators of each at least one further plurality of optical modulators 21 may be adapted for transforming the radiation signal 7 in accordance with a further transfer function corresponding to this at least one further plurality of optical modulators. Each further transfer function may likewise be unique, e.g. may differ from all other further transfer functions, as well as being different from the first transfer function and the second transfer function.

Thus, substantially identical channels may be replicated in a multi-channel spectrometer device in accordance with embodiments. It is an advantage of embodiments of the present invention that thus a high signal to noise ratio can easily and efficiently be achieved by providing multiple simultaneous measurements of each transform component.

A optical modulator in a multi-channel spectrometer device according to embodiments of the present invention may be a photonic resonator, a photonic filter or other integrated photonic circuit component, e.g. a Mach-Zehnder Interferometer, a Fabry-Perot cavity or a resonator ring.

Furthermore, the multi-channel spectrometer device comprises at least one detector element 15 operably connected to the first plurality of optical modulators 12 and to the second plurality of optical modulators 13. This at least one detector element 15 is adapted for generating a plurality of output signals 4 indicative for the intensity of each of the plurality of transformed radiation signals 8 of the first plurality of optical modulators 12 and of each of the plurality of transformed radiation signals 9 of the second plurality of optical modulators 13. Furthermore, the at least one detector element 15 may also be adapted for generating output signals indicative for the intensity of each of the plurality of transformed radiation signals of each of the at least one further plurality of optical modulators 21.

The at least one detector element 15 may comprise a plurality of detector elements, each detector element connected to one corresponding optical modulator of the first plurality of optical modulators, the second plurality of optical modulators or any further plurality of optical modulators, e.g. the detector elements may be one-on-one connected to the optical modulators. Alternatively, the multi-channel spectrometer device may comprise multiplexing means to route the transformed radiation signals of the optical modulators to the at least one detector element, e.g. such as to generate the plurality of output signals by sequentially or block-wise reading out all the transformed radiation signals.

In embodiments of the present invention, the ratio $r=N_1/N_2$ of the number $N_1$ of optical modulators in the first plurality of optical modulators and the number $N_2$ of optical modulators in the second plurality of optical modulators is substantially determined by the ratio $I=I_1/I_2$ of a reference spectrum $S(\lambda)$ of the predetermined analyte of interest transformed by the first transfer function $T_1(\lambda)$ and the reference spectrum transformed by the second transfer function $T_2(\lambda)$. For example, $$I_1 = \int_0^\infty T_1(\lambda) \cdot S(\lambda) d\lambda \text{ and } I_2 = \int_0^\infty T_2(\lambda) \cdot S(\lambda) d\lambda.$$

The ratio $r=N_1/N_2$ may be substantially different from 1, e.g. may be less than 0.9 or higher than 1.1, e.g. may be less than 0.5 or higher than 2, or may even be less than or equal to 0.2 or higher than or equal to 0.8. Thus, one of the first plurality and the second plurality may comprise at least twice the number of optical modulators of the other.

Where reference is made to the first plurality of optical modulators and the second plurality of modulators, the same may equally apply to any plurality of optical modulators in relation to any other plurality of optical modulators, the first plurality of optical modulators and/or the second plurality of modulators. Thus, in embodiments of the present invention, for any pair of pluralities of modulators selected from the first, the second and all further pluralities of optical modulators, the ratio $r=N_i/N_j$ of the number $N_i$ of optical modulators in the first plurality of this pair and the number $N_j$ of optical modulators in the second of this pair is substantially determined by the ratio $I=I_i/I_j$ of a reference spectrum $S(\lambda)$ of the predetermined analyte of interest transformed by the transfer function $T_i(\lambda)$ corresponding to the first plurality of this pair and the reference spectrum transformed by the transfer function $T_j(\lambda)$ corresponding to the second plurality of this pair. For example, the ratio I may be determined as the ratio of $$I_i = \int_0^\infty T_i(\lambda) \cdot S(\lambda) d\lambda \text{ and } I_j = \int_0^\infty T_j(\lambda) \cdot S(\lambda) d\lambda.$$

Furthermore, where hereinbelow reference is made to the first plurality of optical modulators and the second plurality of modulators, the same may equally apply to respectively the first plurality of a pair and the second plurality of this pair for any pair of pluralities of modulators selected from the first, the second and all further pluralities of optical modulators.

Thus, the distribution of channels in the spectrometer device may be tuned to match the transform, e.g. as defined by the set of different transfer functions, of the target spectrum and/or to minimize the impact of known parasitic spectra.

The ratio r may be equal to an integer power of the intensity ratio I, e.g. $(I_1/I_2)^p$ where p may be an integer in the range of −10 to 10, except 0. It will be understood by the person skilled in the art that such considerations are to be interpreted within the limits of rounding errors, e.g. $r=N_1/N_2=I^p$ may be understood as $\min((N_1-1)/N_2, N_1/(N_2+1)) \leq I^p \leq \max((N_1+1)/N_2, N_1/(N_2-1))$, insofar r is not equal to 1.

For example, the ratio of the number of optical modulators in the first plurality of optical modulators and the number of optical modulators in the second plurality of optical modulators may be equal to the intensity ratio of a reference spectrum of the predetermined analyte of interest transformed by the first transfer function and the reference spectrum transformed by the second transfer function. It is an advantage of such dependence that more output signals are generated for basis function components of the acquired spectrum having a relatively high spectral intensity, e.g. to acquire more data for strong signals which may be particularly informative for detecting small concentrations of the analyte of interest in the medium. Thus, key differentiating channels can be the focus of the architecture, e.g. a large replication may be provided for important differentiating channels, e.g. having a relatively high spectral intensity. Furthermore, the ratio of the number of optical modulators in the first plurality of optical modulators and the number of optical modulators in the second plurality of optical modulators may also be equal to a positive integer power, e.g. a square power or a cubic power, of the intensity ratio of a reference spectrum of the predetermined analyte of interest transformed by the first transfer function and the reference spectrum transformed by the second transfer function, e.g. $r=I_1/I_2$, $r=(I_1/I_2)^2$, or $(I_1/I_2)^3$, generally $(I_1/I_2)^p$ where p may be a positive integer smaller or equal to 10, e.g. smaller than or equal to 5.

Alternatively, the ratio of the number of optical modulators in the first plurality of optical modulators and the number of optical modulators in the second plurality of optical modulators may be equal to the intensity ratio of a reference spectrum of the predetermined analyte of interest transformed by the second transfer function and the reference spectrum transformed by the first transfer function. It is an advantage of such dependence that more output signals are generated for basis function components of the acquired spectrum having a relatively low spectral intensity, e.g. to acquire more data for weak signals in order to improve the signal to noise ratio. Thus, channels with low target signal can be replicated in large numbers to boost the signal-to-noise ratio (SNR) from these spectral regions. However, given the quadratic dependence of an averaged signal on the noise component present in its component terms, the ratio of the number of optical modulators in the first plurality of optical modulators and the number of optical modulators in the second plurality of optical modulators may also be equal to the square of the intensity ratio of a reference spectrum of the predetermined analyte of interest transformed by the second transfer function and the reference spectrum transformed by the first transfer function. Moreover, the ratio of the number of optical modulators in the first plurality of optical modulators and the number of optical modulators in the second plurality of optical modulators may also be equal to a negative integer power of the intensity ratio of a reference spectrum of the predetermined analyte of interest transformed by the first transfer function and the reference spectrum transformed by the second transfer function, e.g. $r=(I_1/I_2)^{-1}$, $r=(I_1/I_2)^{-2}$, or $(I_1/I_2)^{-3}$, generally $(I_1/I_2)^{-p}$ where p may be a positive integer smaller or equal to 10, e.g. smaller than or equal to 5.

In a second aspect, the present invention relates to a spectrometer system comprising a spectrometer device, e.g. as shown in FIG. 1. A spectrometer system 25 according to embodiments of the present invention comprises a radiation source 26 for illuminating a medium 6 and a multi-channel spectrometer device 10 for detecting and/or quantifying a predetermined analyte 5 of interest in the medium 6. This multi-channel spectrometer device 10 is a spectrometer device according to embodiments of the first aspect of the present invention. The multi-channel spectrometer device 10 is configured to receive a radiation signal 7 from the illuminated medium 6 via the input 11 of the multi-channel spectrometer device 10. For example, the system 25 may comprise a sample holder for containing the medium 6 during operation, such that when the radiation source 26 illuminates the medium 6, a radiation signal propagates from the medium 6 to the input 11 of the multi-channel spectrometer device 10, thereby spectrally conveying information in the radiation signal 7 about the presence and/or concentration of the predetermined analyte 5 in the medium 6. The spectrometer system 25 may also comprise a processing means 27, e.g. processor, for analyzing the plurality of output signals 4 generated by the at least one detector element 15 of the multi-channel spectrometer device 10. Thus, the processor may be adapted for detecting and/or quantifying the predetermined analyte 5 of interest in the medium 6 by analysing the plurality of output signals generated by the at least one detector element 15.

For example, the spectrometer system 20 may comprise a radiation source 26 such as a device for generating excitation radiation, e.g. a laser diode, such as a laser diode with a frequency-selective element. The multi-channel spectrometer device 10 may be adapted for detecting a Raman spectrum of the medium to be investigated. The spectrometer system 20 may comprise a data processing device, wherein the multi-channel spectrometer device 10 comprises the data processing device or is connected the data processing device. For example, the system may be adapted for producing electromagnetic excitation radiation with a laser diode, coupling the excitation radiation into the medium to be investigated, coupling the electromagnetic radiation scattered by the medium to be investigated into the multi-channel spectrometer device 10 and detecting at least one Raman spectrum from the scattered radiation.

In a third aspect, the present invention also relates to a method for detecting and/or quantifying a predetermined analyte of interest in a medium. This method comprises receiving a radiation signal carrying information about constituents of the medium in its spectral composition and optically modulating the radiation signal to provide a first plurality of transformed radiation signals, wherein each of the first plurality of transformed radiation signals is a transformation of the radiation signal in accordance with a first transfer function. The method further comprises optically modulating the radiation signal to provide a second plurality of transformed radiation signals, wherein each of the second plurality of transformed radiation signals is a transformation of the radiation signal in accordance with a second transfer function, the second transfer function being distinct from the first transfer function. The method also comprises generating a plurality of signals indicative for the intensity of each transformed radiation signal of the first plurality and of the second plurality of transformed radiation signals, and analyzing the plurality of signals to detect and/or quantify the predetermined analyte of interest in the medium. The ratio of the number of transformed radiation signals in the first plurality of transformed radiation signals and the number of transformed radiation signals in the second plurality of transformed radiation signals is substantially determined by the ratio of a reference spectrum of the predetermined analyte of interest transformed by the first transfer function and the reference spectrum transformed by the second transfer function. Thus, the ratio having as numerator the number of transformed radiation signals in the first plurality of transformed radiation signals and as denominator the number of transformed radiation signals in the second plurality of transformed radiation signals is substantially determined by the ratio having a numerator a reference spectrum of the predetermined analyte of interest transformed by the first transfer function and as denominator the reference spectrum transformed by the second transfer function.

Such a method for detecting and/or quantifying a predetermined analyte of interest in a medium according to embodiments may relate to a method for detecting and/or quantifying using a spectrometer device according to the first aspect of the present invention, and/or using a spectrometry system according to the second aspect of the present invention. Features and details of methods according to embodiments of the present invention may be clear from the corresponding description hereinabove relating to the first and/or second aspect of the present invention. Likewise, features and details of a device or system according to the first or second aspect of the present invention may be clear from the corresponding description hereinbelow relating to a method according to embodiments.

Figure 3:
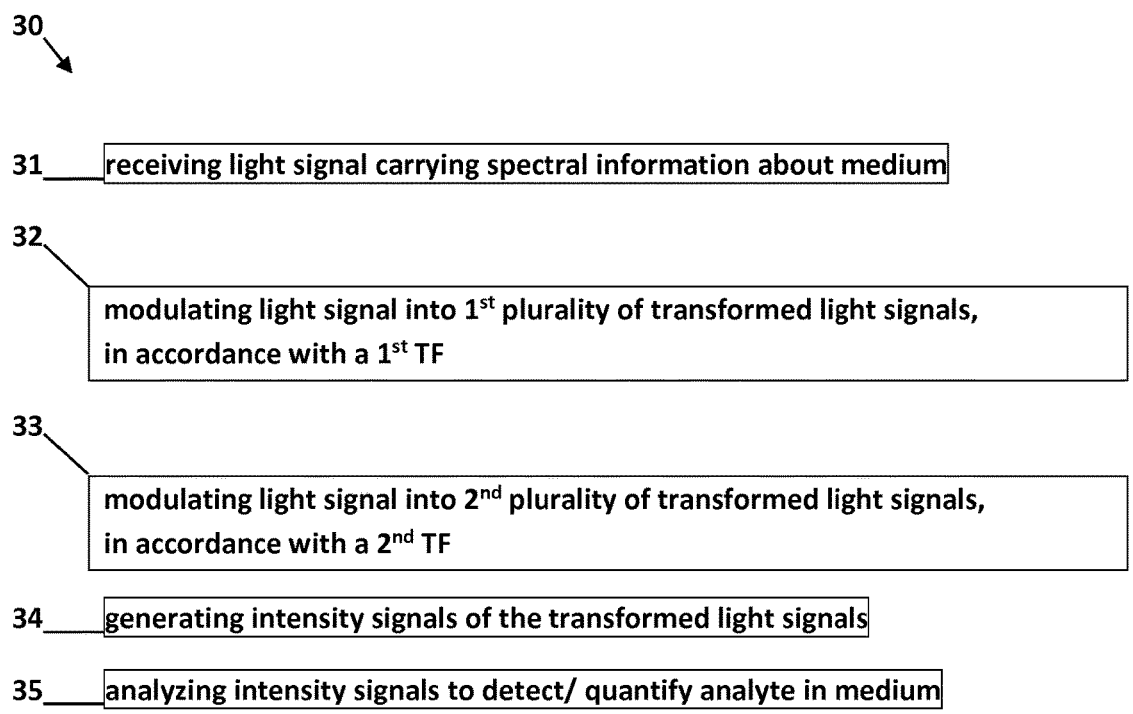
FIG. 3 illustrates an exemplary method for detecting and/or quantifying a predetermined analyte of interest according to embodiments of the present invention.

Referring to FIG. 3, an exemplary method 30 for detecting and/or quantifying a predetermined analyte 5 of interest in a medium 6 is shown. The method 30 comprises receiving 31 a radiation signal 7 carrying information about constituents of the medium 6 in its spectral composition. For example, the method may comprise coupling the radiation signal 7 into a multi-channel spectrometer device 10. The method 30 may also comprise illuminating the medium, e.g. a sample of the medium. This illuminating may comprise impinging a coherent, incoherent or partially coherent radiation wave on the medium, having a monochromatic or polychromatic spectrum, in accordance with the spectrometry technique the embodiment relates to. For example, for Raman spectrometry, a method 30 according to embodiments may comprise illuminating the medium using a laser, e.g. a tunable laser, in the near infrared, visible or near-ultraviolet spectrum. Thus, receiving 31 the radiation signal 7 may comprise collecting radiation from the medium, e.g. the medium sample, at a predetermined angle with respect to the axis along which the medium is illuminated. For example, for Raman spectrometry, this angle may be substantially 135°, 90° or 180° with respect to the laser beam exiting the medium after propagating through the medium. A method 30 according to embodiments of the present invention may be a method for performing multi-channel Raman spectrometry. A method 30 according to embodiments of the present invention may be a method for quantifying the concentration of glucose in blood.

The method 30 further comprises optically modulating 32 the radiation signal 7 to provide a first plurality of transformed radiation signals, each of the first plurality of transformed radiation signals being a transformation of the same radiation signal 7 in accordance with a first transfer function. The method 30 also comprise optically modulating 33 the radiation signal 7 to provide a second plurality of transformed radiation signals, each of the second plurality of transformed radiation signals being a transformation of the radiation signal 7 in accordance with a second transfer function.

The ratio of the number of transformed radiation signals in the first plurality of transformed radiation signals and the number transformed radiation signals in the second plurality of transformed radiation signals is substantially determined by the ratio of a reference spectrum of the predetermined analyte of interest transformed by the first transfer function and the reference spectrum transformed by said second transfer function. Furthermore, the ratio of the number of transformed radiation signals in the first plurality of transformed radiation signals and the number of transformed radiation signals in the second plurality of transformed radiation signals may be substantially equal to, e.g. equal to, an integer power of the ratio of the reference spectrum transformed by the first transfer function and the reference spectrum transformed by the second transfer function, in which this integer power has an integer exponent in the range of $-10$ to $-1$ or in the range of 1 to 10. For example, this integer power may be the identity function or the reciprocal function.

A method 30 according to embodiments may further comprise optically modulating the radiation signal to provide at least one further plurality of transformed radiation signals, each transformed radiation signal of each further plurality of transformed radiation signals being a transformation of the same radiation signal 7 in accordance with a further transfer function corresponding to that further plurality of transformed radiation signals. For example, for each pair of pluralities selected from the first plurality of transformed signals, the second plurality of transformed signals and the or each at least one further plurality of transformed signals, the ratio of the number of transformed radiation signals in the first plurality of this pair and the number transformed radiation signals in the second plurality of this pair may be substantially determined by the ratio of the reference spectrum transformed by the transfer function corresponding to the first plurality of this pair and the reference spectrum transformed by the transfer function corresponding to the second plurality of this pair. "Being substantially determined by" may here also refer to "being substantially equal to, e.g. equal to, an integer power of". This integer power may have an integer exponent in the range of −10 to −1 or in the range of 1 to 10. For example, this integer power may be the identity function or the reciprocal function.

Optically modulating the radiation signal to provide the first, the second and/or the at least one further plurality of transformed radiation signals may comprise splitting the radiation signal 7 into a plurality of substantially identical signal copies to be transformed.

The method 30 further comprises generating 34 a plurality of signals 4 indicative for the intensity of each transformed radiation signal 8 of the first plurality and of the second plurality of transformed radiation signals, and analyzing 35 the plurality of signals 4 to detect and/or quantify the predetermined analyte 5 of interest in the medium.

In a further aspect, the present invention also relates to a method for designing a multi-channel spectrometer device for detecting and/or quantifying a predetermined analyte of interest in a medium. This method comprises obtaining a reference spectrum of the predetermined analyte of interest. The method also comprises selecting a plurality of transfer functions corresponding to a plurality of optical modulators. Further, the method comprises providing a multi-channel spectrometer device design comprising a plurality of optical modulators coupled to an input for receiving a radiation signal, wherein for each pair of transfer functions out of the plurality of transfer functions, the ratio of the number of optical modulators having the first transfer function of this pair and the number of optical modulators having the second transfer function of this pair is determined by the ratio of the reference spectrum transformed by the first transfer function and the reference spectrum transformed by the second transfer function.

Figure 4:
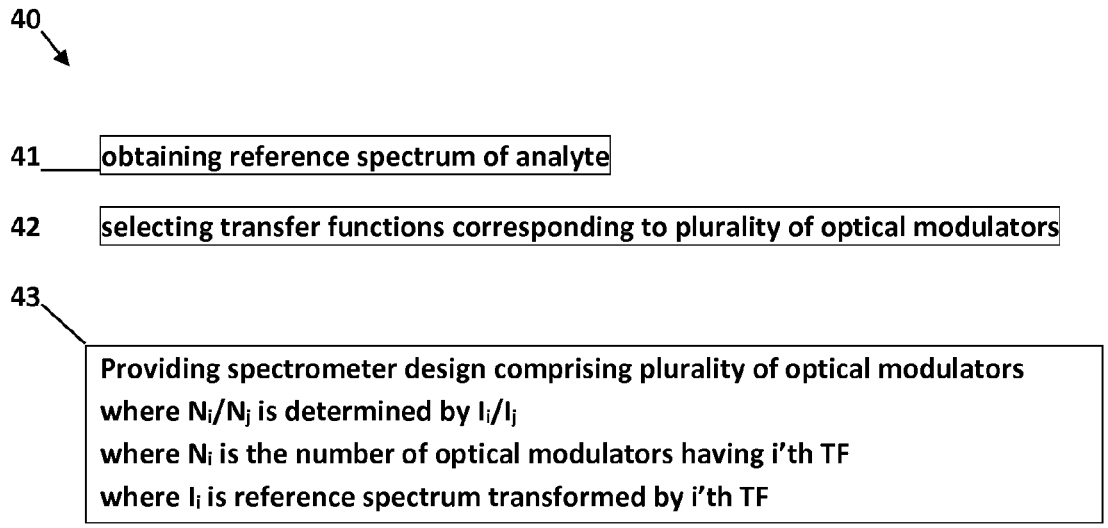
FIG. 4 illustrates a method for designing a multi-channel spectrometer device according to embodiments of the present invention.

FIG. 4 illustrates a method 40 for designing a multi-channel spectrometer device 10 for detecting and/or quantifying a predetermined analyte 5 of interest in a medium 6 according to embodiments of the present invention.

This method 40 comprises obtaining 41 a reference spectrum of the predetermined analyte of interest, e.g. the spectrum of the component one tries to isolate for detection and/or quantification.

This method 40 also comprises selecting 42 a plurality of transfer functions corresponding to a plurality of optical modulators. These transfer functions may correspond to mutually unique channels of the multi-channel spectrometer being designed. For example, a transfer function may correspond to a photonic resonator, a photonic filter or other integrated photonic circuit component. For example, a transfer function may correspond to a Mach-Zehnder Interferometer, a Fabry-Perot cavity, a resonator ring, a stub and/or a combination of such structures.

The method 40 may comprise selecting 42 the plurality of transfer functions taking into account a spectral range of interest for detecting or quantifying the analyte of interest. Selecting 42 the plurality of transfer functions taking into account the reference spectrum may comprise selecting the plurality of transfer functions of the different channels of the transform spectrometer to form or approximate a basis of functions. For example selecting 42 the plurality of transfer functions may comprise selecting a minimal set of orthogonal functions which combination allows reproducing any arbitrary spectrum in the wavelength range of interest, with a predetermined accuracy.

The method 40 may comprise selecting 42 the plurality of transfer functions taking into account the reference spectrum. For example, the distribution of the mutually unique channels of the multi-channel spectrometer can be optimized for the spectrum of the component one tries to isolate. Thus, while the multi-channel spectrometer may be less suitable for general spectrometry purposes, e.g. detecting unspecified analytes, it may advantageously provide a good performance in detection or quantification of a specific predetermined analyte.

Thus, the transformation implemented by the multi-channel spectrometer can be selected so as to form an optimal function basis for the detection of a target quantity. From this basis, a limited set to best match the spectrum of interest can be selected. For example, one basis function may be totally useless to assess a given target spectrum, and thus may be removed from the selection. The optimized basis can be comprise the principal axes of the spectrum, on may be determined by another numerical detection algorithm.

For example, selecting the plurality of transfer functions taking into account the reference spectrum may comprise a principal component analysis, a genetic algorithm optimization, a least squares optimization, such as ordinary least squares or total least squares, a lasso algorithm, a kernel learning method optimization, or another optimization method known in the art. Furthermore, a plurality of reference spectra may be taken into account, e.g. corresponding to a plurality of concentrations of the analyte of interest in the medium, e.g. a calibration batch, and/or corresponding to a plurality of differently composed media, e.g. a set of background media. For example, if the analyte of interest in the medium is a glucose blood sample, reference spectra may be obtained for different concentrations of glucose, as well as for different concentrations of other blood components in the medium.

Selecting 42 the plurality of transfer functions taking into account the reference spectrum may comprise selecting an optimal function basis for the detection of the target analyte quantity. Selecting 42 the plurality of transfer functions may furthermore comprise selecting a limited set to best match the spectrum of interest, e.g. to realize an identification algorithm at least partly in the optical domain.

The method 40 further comprises providing 43 a multi-channel spectrometer device design comprising a plurality of optical modulators coupled to an input 11 for receiving a radiation signal 7. For each pair of transfer functions out of the plurality of transfer functions, the ratio of the number of optical modulators having the first transfer function of this pair and the number of optical modulators having the second transfer function of this pair is determined by the ratio of the reference spectrum transformed by the first transfer function and the reference spectrum transformed by the second transfer function. Thus, the signal to noise ratio for detection and quantification of the analyte of interest can be advantageously increased by replicating identical channels in the spectrometer in accordance with the distribution determined by the reference spectrum projected through the plurality of transfer functions. Thus, key differentiating channels can be the focus of the architecture, e.g. providing large replication of key differentiating channels. Alternatively, channels with low target signal, e.g. low information photon count, can be replicated in large numbers to boost the signal to noise ratio from these spectral regions.

The present invention also relates to a computer program product for implementing a method 40 according to embodiments of the present invention, when executing on a computing device.

Figure 5:
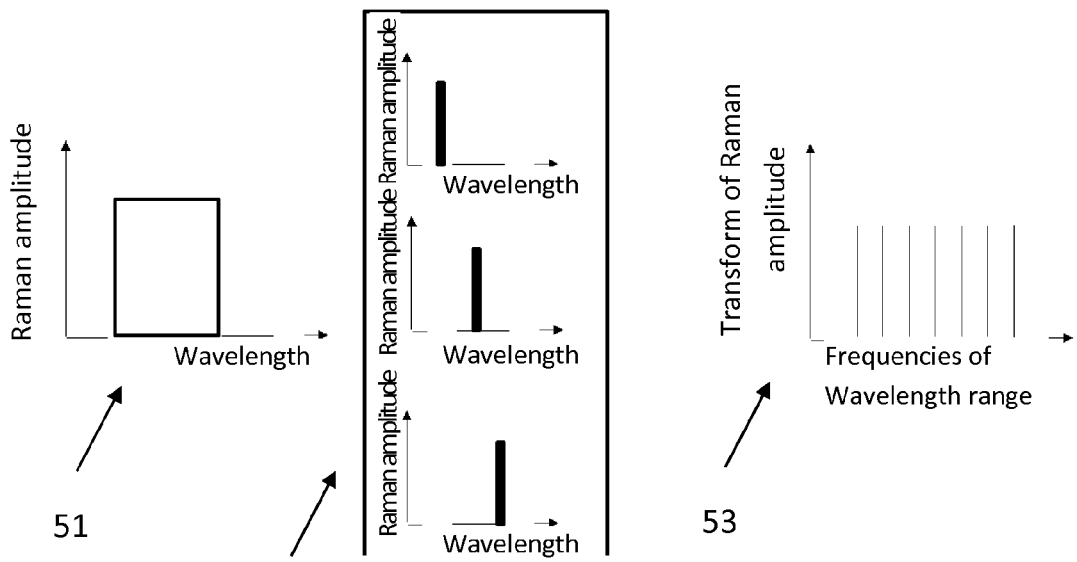
FIG. 5 illustrates aspects of designing a multi-channel spectrometer according to embodiments of the present invention.

Aspects of embodiments of the present invention are illustrated by FIG. 5 to FIG. 9. For example, FIG. 5 illustrates steps relating to an exemplary method for designing a multi-channel spectrometer according to embodiments of the present invention. The analyte of interest may have a corresponding wavelength range 51 of interest, e.g. a range known to be suitable for detecting the analyte and/or determined by the spectroscopy technology confounding factors. A discrete basis 52 may be selected of basis functions, e.g. corresponding to transfer functions of Fabry-Perot cavity resonators. If the wavelength range 51 were to be assessed uniformly, e.g. without taking prior knowledge of the analyte of interest into account other than for defining the spectral range 51, the projection 53 of a uniform function over the wavelength range 51 through the selected discrete basis can be used to define a corresponding distribution of Fabry-Perot cavity lengths. Thus the basis functions may comprise narrow band-pass functions around a wavelength determined by the effective cavity dimensions.

Figure 6:
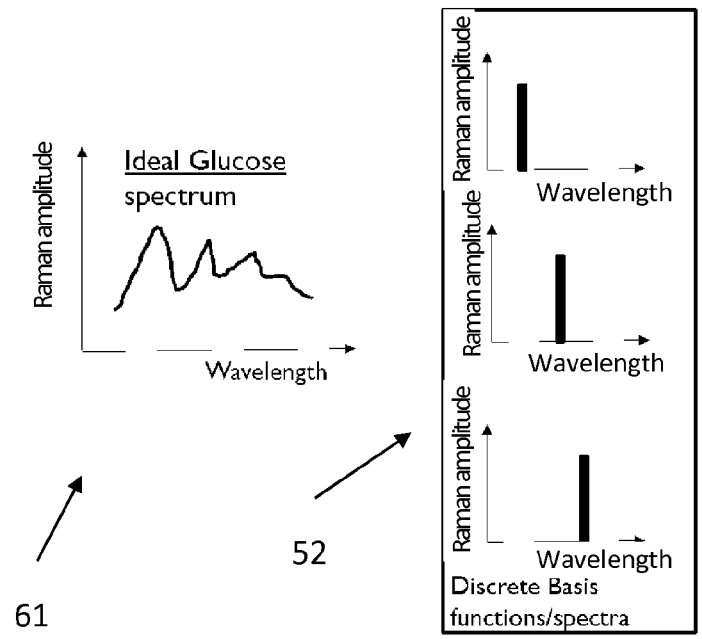
FIG. 6 illustrates a reference spectrum of the analyte of interest in relation to aspects of designing a multi-channel spectrometer according to embodiments of the present invention.

However, referring to FIG. 6, the analyte of interest may have a reference spectrum 61 that can be taken into account. Due to this non-uniform information distribution in the wavelength range 51, also a non-uniform signal to noise ratio can be expected over this range when detecting and/or quantifying the analyte of interest. Thus, the discrete basis 52 may also be sub-optimal for detecting the analyte of interest. However, in accordance with embodiments of the present invention, the performance for detecting and quantifying the analyte can be boosted by selecting the more relevant basis components and replicating these in the spectrometer device. For example, the same number of channels as would be used in a general purpose implementation, e.g. in accordance with the principles shown in FIG. 5, can be used more efficiently for the specific purpose of detecting a particular analyte, e.g. glucose. For example, a reference spectrum of the analyte of interest, in accordance with the intended spectrometry technique, when transformed by the basis functions shown in FIG. 5, can be used to determine the distribution of Fabry-Perot lengths.

Figure 7:
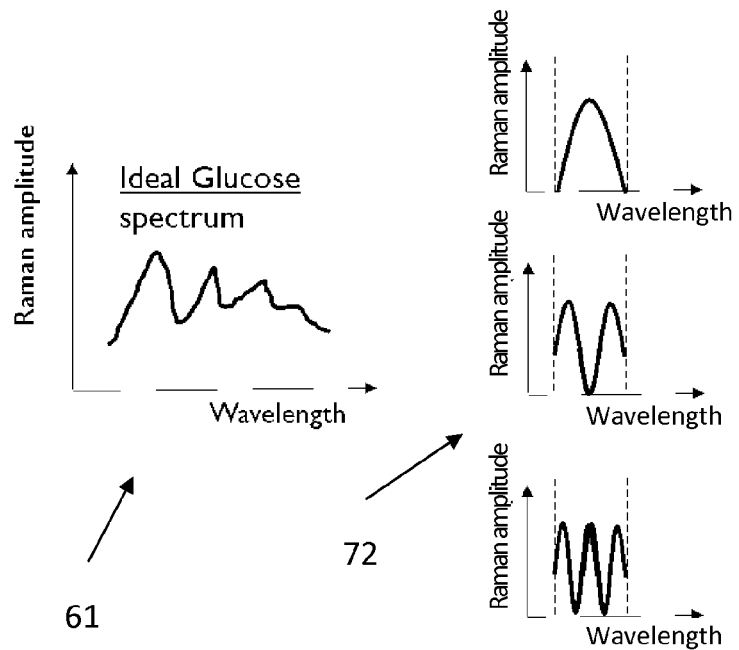
FIG. 7 illustrates the use of the reference spectrum to determine an optimized set of transfer functions relating to aspects of designing a multi-channel spectrometer according to embodiments of the present invention.

Furthermore, the basis functions can also be specifically selected as function of the analyte to be detected. For example, as illustrated in FIG. 7, the reference spectrum 61 of the analyte of interest can be used to determine a set of transfer functions which is optimized for specifically detecting the analyte of interest. For example, Tarumi et al., "Multivariate calibration with basis functions derived from optical filters," Anal. Chem. 2009, 81, 2199-2207, discloses a numerical optimization method known in the art, which can be used to define a set of Gaussian basis functions for representing the important information in a calibration set of near-IR spectra.

Figure 8:
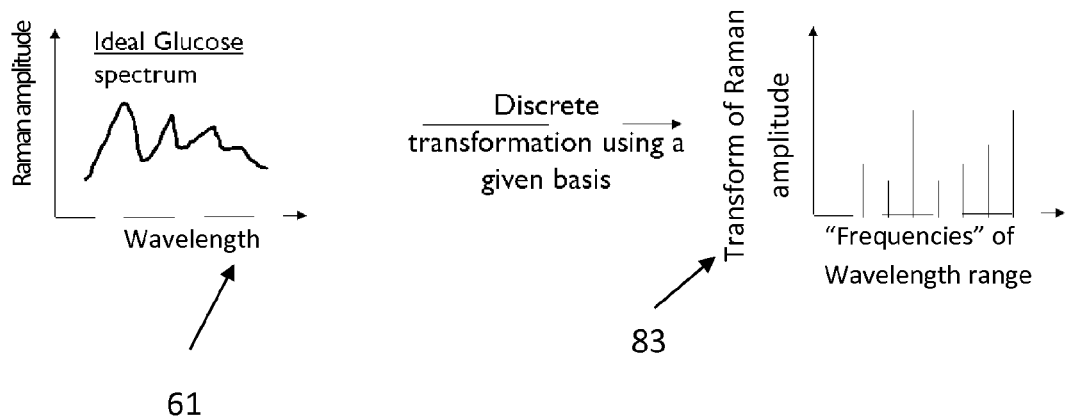
FIG. 8 illustrates a discrete transformation of the reference spectrum relating to aspects of designing a multi-channel spectrometer according to embodiments of the present invention.
Figure 9:
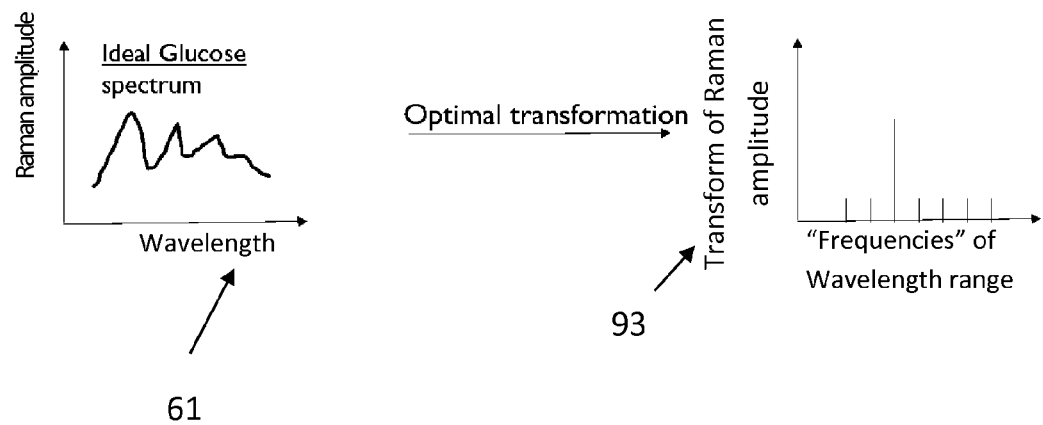
FIG. 9 illustrates an optimized transformation of the reference spectrum relating to aspects of designing a multi-channel spectrometer according to embodiments of the present invention.

FIG. 8 shows how the discrete transformation of the reference spectrum 61 via a predetermined basis yields a transformed histogram 83 of reference spectrum components corresponding to each basis function. This transformed histogram may then be used, in accordance with embodiments of the present invention, to steer the distribution of physical channels in a multi-channel spectrometer device targeting each component of the target analyte spectrum, e.g. a glucose spectrum under the predetermined basis. Furthermore, FIG. 9 shows how an optimal transformation, e.g. via a basis determined via principal axes or key defining features of the reference spectrum 61, defines a set of components to be assessed in the optical domain. The discrete transformation of the reference spectrum 61 via this optimized basis yields a transformed histogram 93 of reference spectrum components corresponding to each basis function. This transformed histogram may then be used, in accordance with embodiments of the present invention, to steer the distribution of physical channels in a multi-channel spectrometer device targeting each component of the target analyte spectrum, e.g. a glucose spectrum under the predetermined basis.

The invention claimed is:

1. A multi-channel spectrometer device for detecting and/or quantifying a predetermined analyte of interest in a medium, the spectrometer device comprising:
   an input for receiving a radiation signal,
   a first plurality of optical modulators operably connected to the input, wherein each optical modulator of the first plurality of optical modulators receives the radiation signal from the input and transforms the radiation signal in accordance with a first spectral transfer function into a plurality of transformed radiation signals of the first plurality of optical modulators, wherein the first spectral transfer function for each of the first plurality of optical modulators is the same, wherein the transformations of the radiation signal by the first plurality of optical modulators occurs within the boundaries of the first plurality of optical modulators;
   a second plurality of optical modulators operably connected to the input, wherein each optical modulator of the second plurality of optical modulators receives the radiation signal from the input and transforms the radiation signal in accordance with a second spectral transfer function into a plurality of transformed radiation signals of the second plurality of optical modulators, wherein the transformations of the radiation signal by the second plurality of optical modulators occurs within the boundaries of the second plurality of optical modulators, wherein the second spectral transfer function for each of the second plurality of optical modulators is the same, wherein the second spectral transfer function is different from the first spectral transfer function, and wherein the radiation signal received by the first plurality of optical modulators is identical to the radiation signal received by the second plurality of optical modulators; and
   at least one detector element operably connected to the first and second plurality of optical modulators, wherein the at least one detector element generates a plurality of output signals indicative of an intensity of each of the plurality of transformed radiation signals of the first and the second plurality of optical modulators, wherein a ratio of the number of optical modulators in the first plurality of optical modulators and the number of optical modulators in the second plurality of optical modulators is substantially determined by a ratio of intensities of a reference spectrum of the predetermined analyte of interest transformed by the first spectral transfer function and the reference spectrum transformed by the second spectral transfer function.

2. The multi-channel spectrometer device according to claim 1, wherein the ratio of the number of optical modulators in the first plurality of optical modulators and the number of optical modulators in the second plurality of optical modulators is substantially equal to an integer power of the ratio of the reference spectrum transformed by the first spectral transfer function and the reference spectrum transformed by the second spectral transfer function, wherein the integer power lies in the range of −10 to −1 or in the range of 1 to 10.

3. The multi-channel spectrometer device according to claim 2, wherein the integer power is an identity function or a reciprocal function.

4. The multi-channel spectrometer device according to claim 1, further comprising at least one further plurality of optical modulators, wherein the optical modulators of the at least one further plurality of optical modulators are adapted for transforming the radiation signal in accordance with a further spectral transfer function.

5. The multi-channel spectrometer device according to claim 1, wherein the multi-channel spectrometer device is a multi-channel Raman spectrometer.

6. The multi-channel spectrometer device according to claim 1, wherein the input comprises a radiation coupler for coupling the radiation signal into the multi-channel spectrometer device.

7. The multi-channel spectrometer device according to claim 1, furthermore comprising a splitter for splitting the radiation signal received by the input into a plurality of waveguides, each waveguide feeding the radiation signal into a corresponding optical modulator.

8. The multi-channel spectrometer device according to claim 1, wherein the first spectral transfer function is determined based on a reference spectrum of glucose, such that the multi-channel spectrometer device is specifically adapted for quantifying a concentration of glucose in blood.

9. The multi-channel spectrometer device according to claim 1, wherein the first plurality of optical modulators, the second plurality of optical modulators, or both comprise a photonic resonator or a photonic filter.

10. The multi-channel spectrometer device according to claim 9, wherein the photonic resonator comprises a Mach-Zehnder Interferometer, a Fabry-Perot cavity or a resonator ring.

11. A spectrometer system comprising:
a radiation source for illuminating a medium and
the multi-channel spectrometer device for detecting and/or quantifying a predetermined analyte of interest in the medium according to claim 1, wherein the multi-channel spectrometer device is configured to receive a radiation signal from the illuminated medium via the input of the multi-channel spectrometer device.

12. The spectrometer system according to claim 11, further comprising a processing means for analyzing the plurality of output signals generated by the at least one detector element of the multi-channel spectrometer device, thereby detecting and/or quantifying the predetermined analyte of interest in the medium.

13. The multi-channel spectrometer device according to claim 1, wherein the ratio ($r=N_1/N_2$) of the number ($N_1$) of optical modulators in the first plurality of optical modulators and the number ($N_2$) of optical modulators in the second plurality of optical modulators is substantially determined by an intensity ratio ($I=I_1/I_2$) of the reference spectrum ($S(\lambda)$) of the predetermined analyte of interest transformed by the first transfer function ($T_1(\lambda)$) and the reference spectrum transformed by the second transfer function ($T_2(\lambda)$),
wherein $$I_1 = \int_0^\infty T_1(\lambda) \cdot S(\lambda) d\lambda \text{ and } I_2 = \int_0^\infty T_2(\lambda) \cdot S(\lambda) d\lambda.$$

14. The multi-channel spectrometer device according to claim 13, wherein the ratio ($r$) is equal to an integer power of the intensity ratio ($I=(I_1/I_2)^p$), wherein p is an integer in the range of −10 to 10, except 0.

15. The multi-channel spectrometer device according to claim 1, wherein the first plurality of optical modulators comprises at least twice the number of optical modulators as the second plurality of optical modulators.

16. A method for detecting and/or quantifying a predetermined analyte of interest in a medium, the method comprising:
receiving, at each optical modulator of a first plurality of optical modulators, a radiation signal carrying information about constituents of the medium in its spectral composition, wherein each optical modulator of the first plurality of optical modulators transforms the radiation signal in accordance with a first spectral transfer function into a first plurality of transformed radiation signals of the first plurality of optical modulators, wherein the first spectral transfer function for each of the first plurality of optical modulators is the same, wherein the transformations of the radiation signal by the first plurality of optical modulators occur within the boundaries of the first plurality of optical modulators;
receiving, at each optical modulator of a second plurality of optical modulators, the radiation signal, wherein each optical modulator of the second plurality of optical modulators transforms the radiation signal in accordance with a second spectral transfer function into a second plurality of transformed radiation signals of the second plurality of optical modulators, wherein the transformations of the radiation signal by the second plurality of optical modulators occur within the boundaries of the second plurality of optical modulators, wherein the second spectral transfer function for each of the second plurality of optical modulators is the same, wherein the second spectral transfer function is different from the first spectral transfer function, and wherein the radiation signal received by the first plurality of optical modulators is identical to the radiation signal received by the second plurality of optical modulators;
generating a plurality of signals indicative of an intensity of each transformed radiation signal of the first plurality and the second plurality of transformed radiation signals; and
analyzing the plurality of signals to detect and/or quantify the predetermined analyte of interest in the medium, wherein a ratio of the number of transformed radiation signals in the first plurality of transformed radiation signals and the number transformed radiation signals in the second plurality of transformed radiation signals is substantially determined by a ratio of intensities of a reference spectrum of the predetermined analyte of interest transformed by the first spectral transfer function and the reference spectrum transformed by the second spectral transfer function.

17. A method for designing a multi-channel spectrometer device for detecting and/or quantifying a predetermined analyte of interest in a medium, the method comprising:
    obtaining a reference spectrum of the predetermined analyte of interest;
    selecting a first and second spectral transfer function corresponding to a first and second plurality of optical modulators, wherein the first spectral transfer function for each of the first plurality of optical modulators is the same, wherein the second spectral transfer function for each of the second plurality of optical modulators is the same, and wherein the second spectral transfer function is different from the first spectral transfer function; and
    providing a multi-channel spectrometer device design comprising the first and second plurality of optical modulators coupled to an input for receiving a radiation signal, wherein the radiation signal received by the first plurality of optical modulators is identical to the radiation signal received by the second plurality of optical modulators, wherein transformations of the radiation signal by the first plurality of optical modulators occur within the boundaries of the first plurality of optical modulators, wherein transformations of the radiation signal by the second plurality of optical modulators occur within the boundaries of the second plurality of optical modulators, and wherein for the first and second spectral transfer functions, a ratio of the first plurality of optical modulators and the second plurality of optical modulators is determined by a ratio of intensities of the reference spectrum transformed by the first transfer function and the reference spectrum transformed by the second transfer function.

18. The method according to claim 17, wherein the input comprises a radiation coupler for coupling the radiation signal into the multi-channel spectrometer device.

19. The method according to claim 17, wherein glucose is the analyte of interest.

20. The method according to claim 17, wherein the plurality of optical modulators comprises a photonic resonator or a photonic filter.

21. The method according to claim 20, wherein the photonic resonator comprises a Mach-Zehnder Interferometer, a Fabry-Perot cavity or a resonator ring.

22. The method according to claim 17, wherein the method is implemented by a computing device.

23. The method of claim 17, wherein the multi-channel spectrometer device is a multi-channel Raman spectrometer.

* * * * *